US00PP36454P3

(12) United States Plant Patent
Choi

(10) Patent No.: US PP36,454 P3
(45) Date of Patent: Feb. 18, 2025

(54) STRAWBERRY PLANT NAMED 'HongHui'

(50) Latin Name: ***Fragaria* x *ananassa***
Varietal Denomination: HongHui

(71) Applicant: Zordi, Inc., Boston, MA (US)

(72) Inventor: Iyeoung Choi, Hongseong (KR)

(73) Assignee: Zordi, Inc., Boston, MA (US)

( * ) Notice: Subject to any disclaimer, the term of this patent is extended or adjusted under 35 U.S.C. 154(b) by 0 days.

(21) Appl. No.: 18/176,716

(22) Filed: Mar. 1, 2023

(65) Prior Publication Data

US 2024/0298556 P1 Sep. 5, 2024

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

PUBLICATIONS

Japanese Plant Variety Protection Registration No. 21165, Issued Oct. 5, 2011, Variety Tokun, Crop Name Strawberry, Applicant National Agriculture and Food Research Organization, 6 pages (English Abstract and Machine Translation).
South Korean Plant Variety Protection Application No. 2016-319, Issued Sep. 28, 2018, Variety Kingsberry, Crop Name Strawberry, Applicant Chungcheongnam-do, 11 pages (English Abstract and Machine Translation).
South Korean Plant Variety Protection Certificate No. 2012-427, Issued Sep. 29, 2014, Variety Sulhyang, Crop Name Strawberry, Applicant Chungcheongnam-do, 10 pages (English Abstract and Machine Translation).
South Korean Plant Variety Protection Certificate No. 2013-9, Issued Feb. 7, 2017, Variety Tokun, Crop Name Strawberry, Applicant National Agriculture and Food Research Organization, 12 pages (English Abstract and Machine Translation).

*Primary Examiner* — Kent L Bell
(74) *Attorney, Agent, or Firm* — MORRISON & FOERSTER LLP

(57) ABSTRACT

A new and distinct variety of strawberry plant named 'HongHui', particularly selected for its very large fruit size, strong fruit glossiness, aroma, juiciness, and very early and consistent flowering, is disclosed.

6 Drawing Sheets

Latin name:
Botanical classification: *Fragaria* x *ananassa*.
Varietal denomination: The varietal denomination of the claimed variety of strawberry plant is 'HongHui'.

BACKGROUND OF THE INVENTION

Cultivated strawberry is a hybrid species of the genus *Fragaria* that is grown worldwide for its fruit. Modern strawberry was first bred in Brittany, France, in the 18th century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'HongHui'.

Strawberry plant variety 'HongHui' originated from a cross made in 2016 between the proprietary female parent 'H2' (itself a hybrid between peach-flavored 'Tokun' (South Korean Plant Variety Protection Certificate No. 2013-9; Japanese Plant Variety Protection Registration No. 21165) and 'Sulhyang' (South Korean Plant Variety Protection Certificate No. 2012-427)) and the male parent variety 'Kingsberry' (South Korean Plant Variety Protection Application No. 2016-319). In 2017, 250 progeny plants from this initial cross were propagated and selected for excellent fruit quality and unique scent. Selected plants were propagated via stolons and underwent further testing for two years (2018-2019). After a cultivation test in Hongseong, South Korea in 2019, variety 'HongHui' was specifically identified and selected. 'HongHui' was subsequently asexually propagated via stolon cuttings, and underwent further testing in Hongseong, South Korea for four months (December 2019-March 2020). The present variety has been found to be stable and reproduce true to type through successive propagations via stolon cuttings.

'HongHui' was selected for its very large fruit size, strong fruit glossiness, aroma, juiciness, and its very early and consistent flowering. The early timing of its consistent flowering and its excellent, vigorous growth enables high yield early in the growing season.

DESCRIPTION OF THE DRAWINGS

This new strawberry plant is illustrated by the accompanying photographs. The colors shown are as true as can be reasonably obtained by conventional photographic procedures. Unless otherwise indicated, the photographs are of plants that are 6-8 months old.

FIG. 1A shows four whole, immature, green fruit of the variety at multiple developmental stages. FIG. 1B shows two whole, immature fruit of the variety, including one fruit that is beginning to redden (right). FIG. 1C shows three whole, immature fruit of the variety; this includes one green fruit (left), one fruit beginning to redden (behind), and one fruit almost fully reddened (right).

DETAILED BOTANICAL DESCRIPTION

Figure 1A:
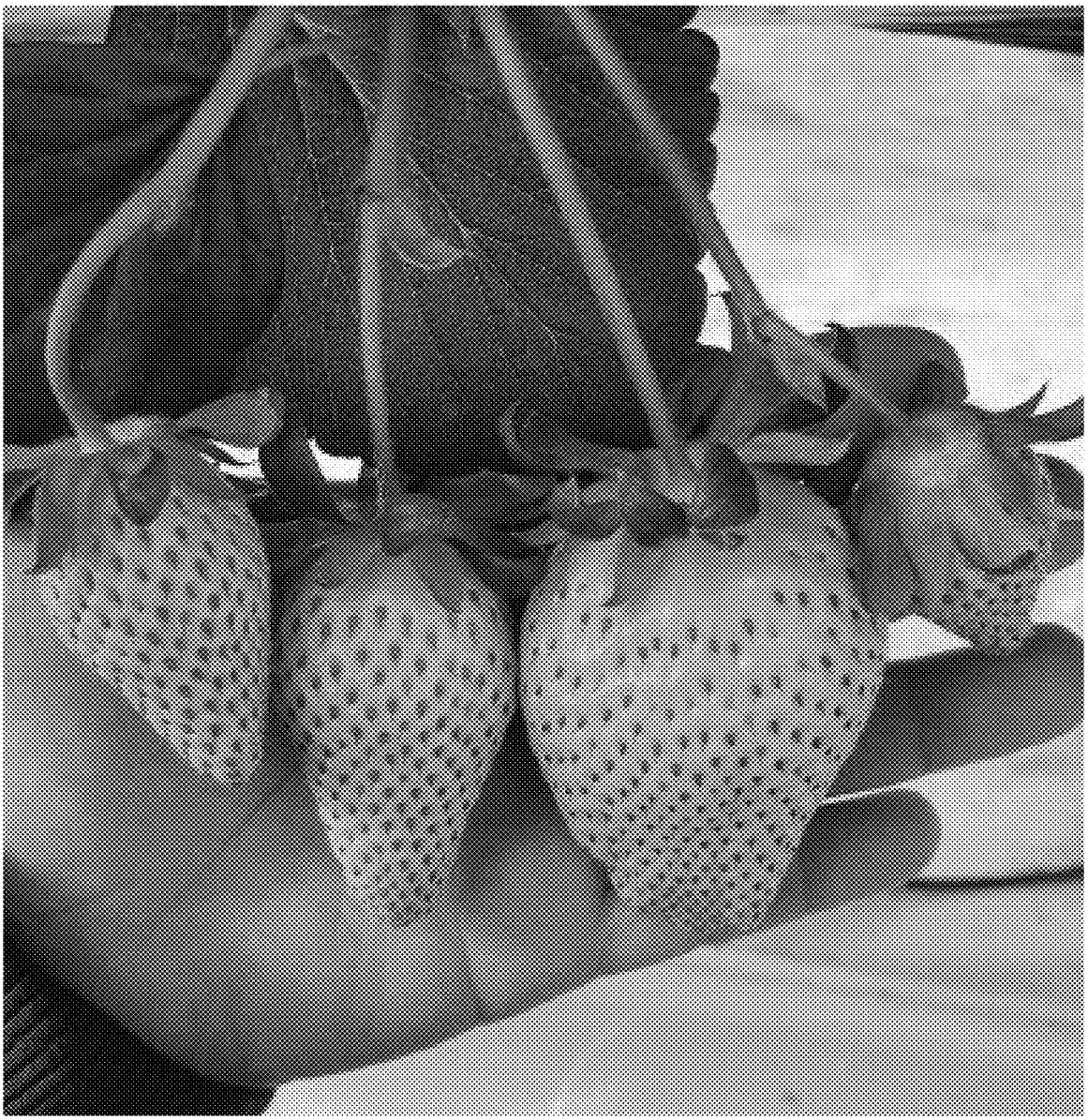
FIGS. 1A-1C illustrate a series of developing fruit of the variety 'HongHui'.
Figure 1B:
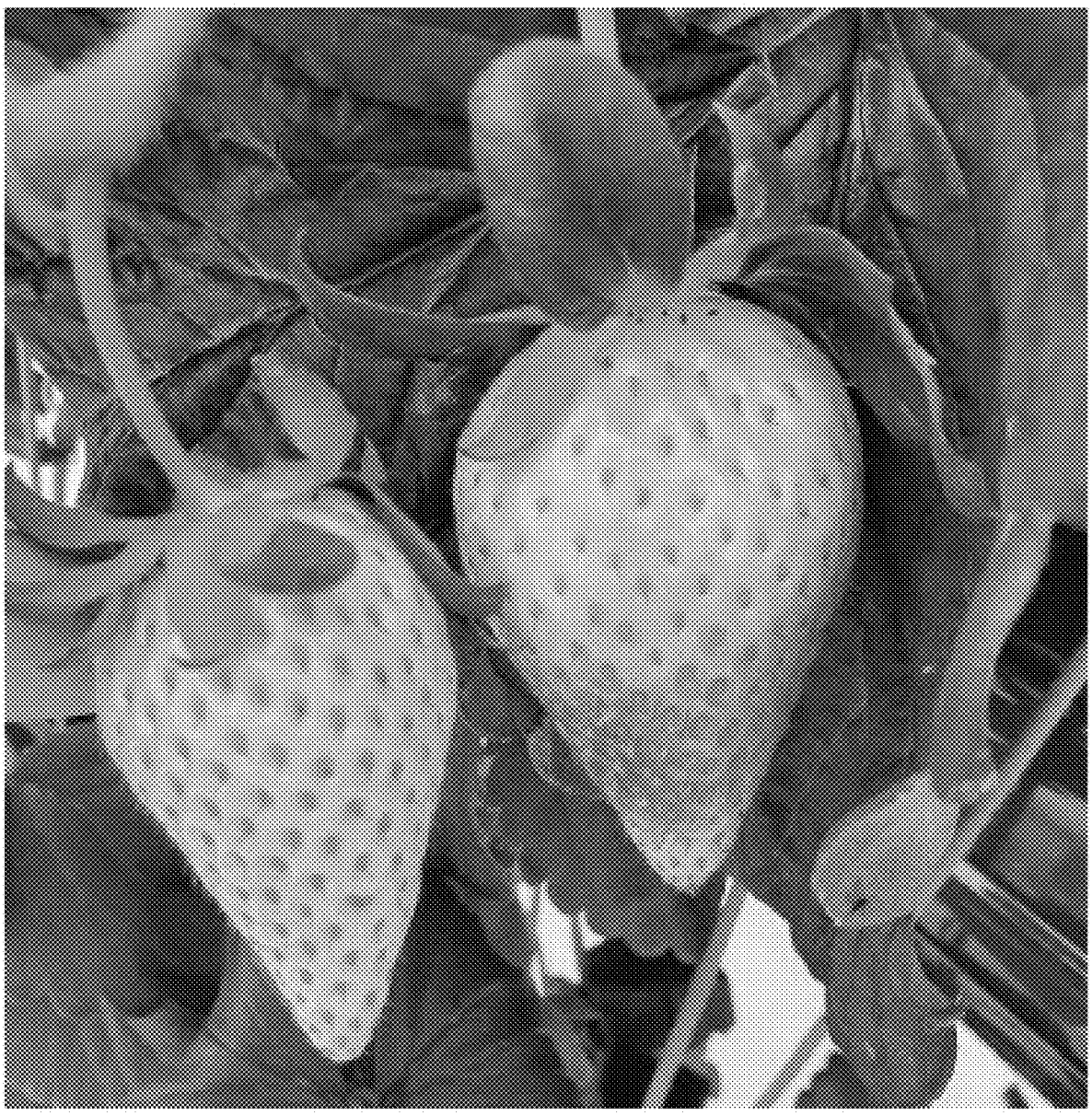
Figure 1C:
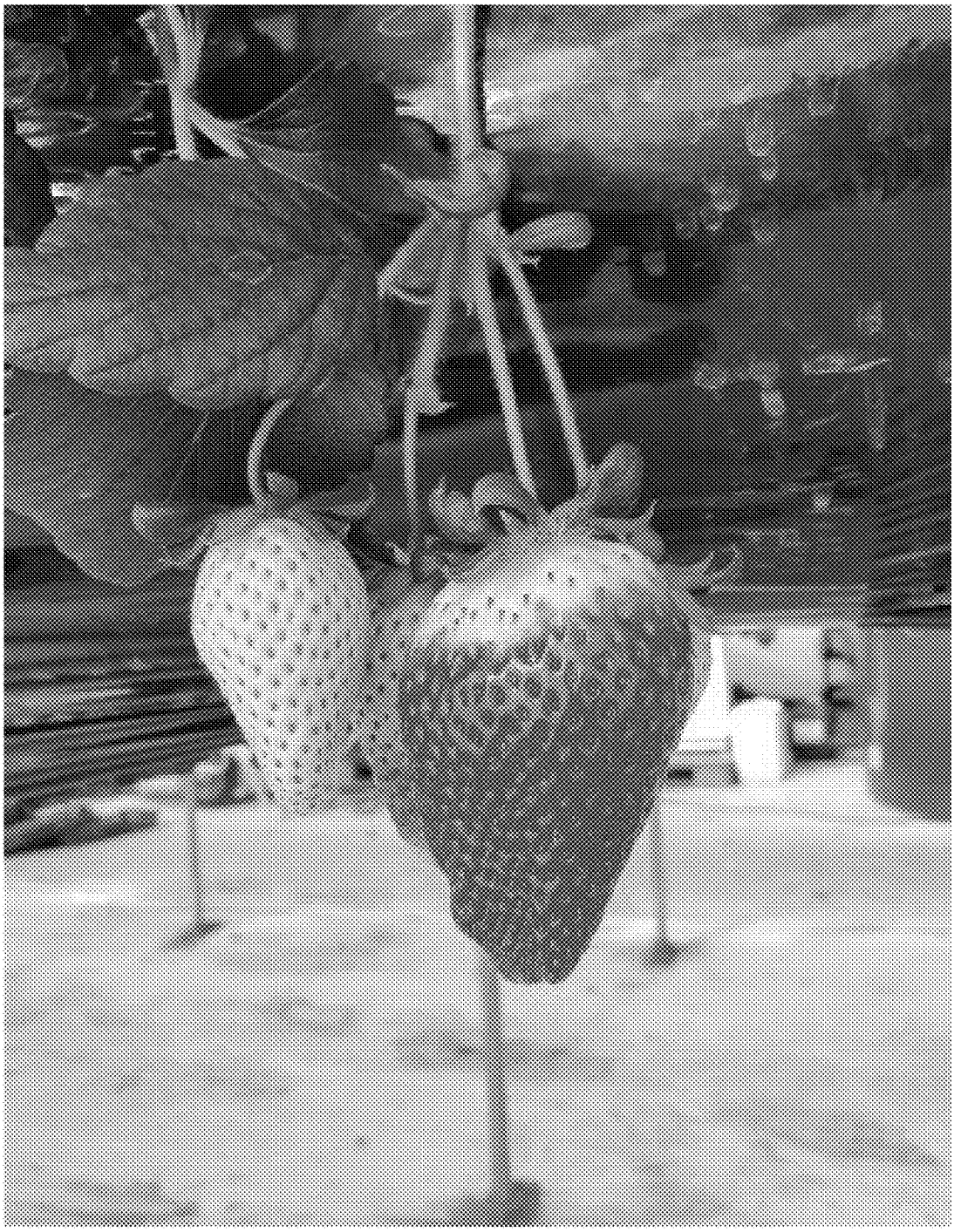
Figure 2:
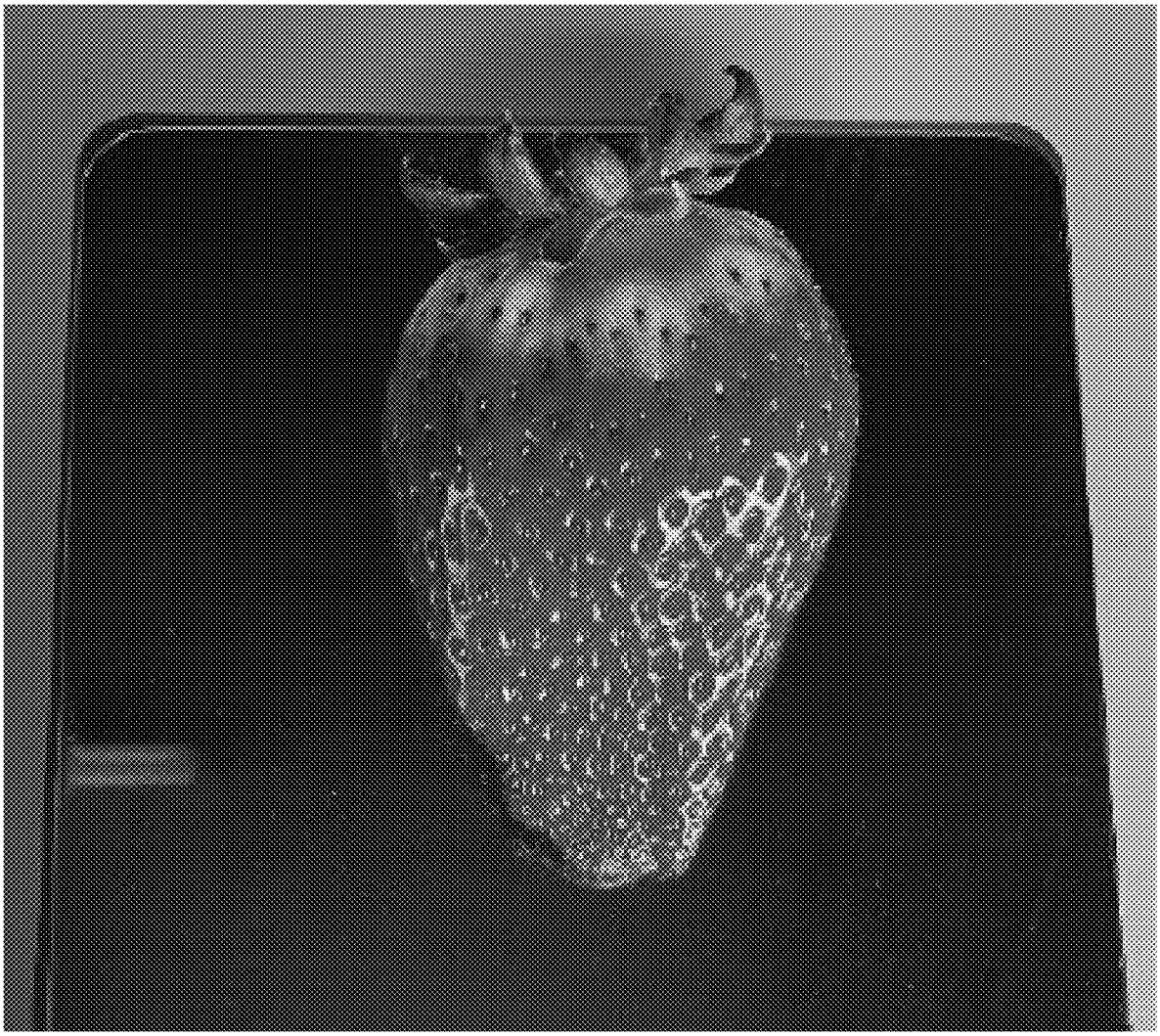
FIG. 2 illustrates a whole mature fruit of the variety 'HongHui', displaying its high glossiness and the outward attitude of the sepals.
Figure 3:
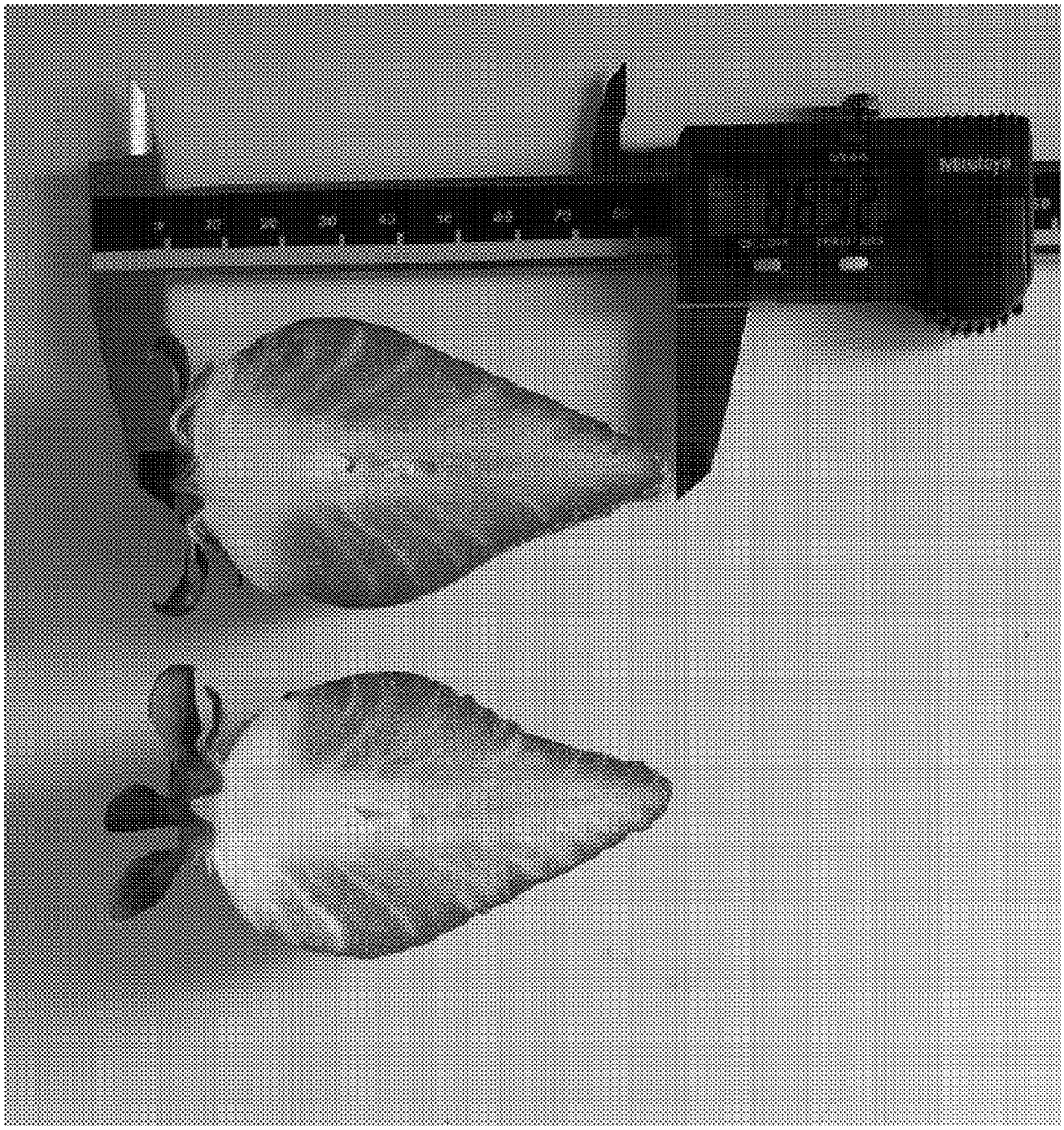
FIG. 3 illustrates longitudinal fruit sections of a mature fruit of the variety 'HongHui' and a measurement of the maximum fruit length (86.32 mm).
Figure 4:
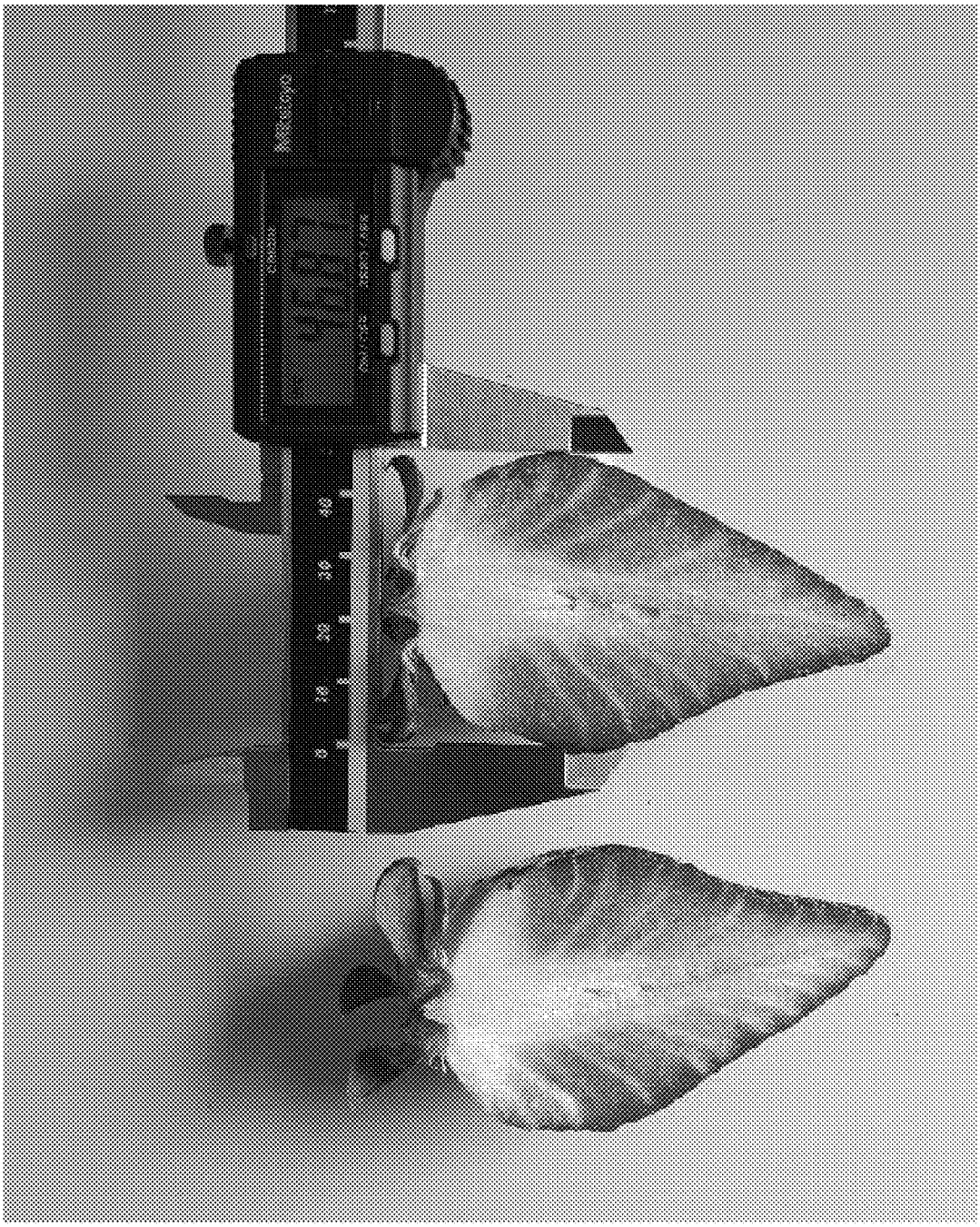
FIG. 4 illustrates a transversal measurement of a longitudinal fruit section of a mature fruit of the variety 'HongHui' and a measurement of the maximum fruit diameter (46.87 mm).

The following detailed description sets forth the distinctive characteristics of 'HongHui'. The data which define these characteristics is based on observations taken in Hongseong, South Korea from December 2019 to March 2020. This description is in accordance with UPOV terminology. Color designations, color descriptions, and other phenotypical descriptions may deviate from the stated values and descriptions depending upon variation in environmental, seasonal, climatic, and cultural conditions. 'HongHui' has not been observed under all possible environmental conditions. The botanical description of 'HongHui' was taken from plants that were 6-8 months old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Genus/species.*—*Fragaria* x*ananassa.*
*Common name.*—Strawberry.
*Denomination.*—'HongHui'.

Parentage:

*Female parent.*—'H2' (unpatented).
*Male parent.*—'Kingsberry' (South Korean Plant Variety Protection Application No. 2016-319).

Plant:

*Number of stolons per plant.*—25.
*Growth habit.*—Upright to semi-upright.
*Density of foliage.*—Medium.
*Vigor.*—Strong.
*Measured height.*—35.7 cm.
*Width/spread.*—31 cm.
*Type.*—Short day.
*U.S.D.A. hardiness zone.*—7a-10b (best for 9a).
*Fusarium wilt resistance.*—Strong.
*Anthracnose resistance.*—Strong.
*Root color.*—White.
*Time to initiate roots.*—3 days.
*Time to produce a rooted plant.*—10 days.

Stolon:

*Length.*—315 mm.
*Diameter.*—5.1 mm.
*Texture.*—Smooth.
*Stolon color.*—RHS 146A (Moderate olive green).
*Anthocyanin coloration.*—Weak.
*Anthocyanin color.*—RHS 182A (Moderate red).

Leaf:

*Size.*—Very large.
*Length.*—14-15 cm.
*Width.*—13-14 cm.
*Division.*—Compound; 3 leaflets.
*Arrangement.*—Spiral.
*Blistering.*—Medium.
*Glossiness.*—Medium.
*Terminal leaflet.*—Shape: Obtuse. Length: 14-15 cm. Width: 13-14 cm. Length/width ratio: Medium. Shape of apex: Serrate to crenate. Shape of base: Acute. Margin: Serrate to crenate. Number of teeth per leaflet: 17. Margin incision depth: Shallow. Shape in cross section: Straight. Color of leaf upper surface: RHS 139A (Dark yellowish green). Color of leaf lower surface: RHS 147B (Moderate yellow green). Texture of upper surface: Rough. Texture of lower surface: Soft. Venation: Pattern: Pinnate. Color: RHS 147A (Moderate olive green).
*Petiole.*—Leaflets: Long. Length: Long; 12 cm. Width: 4 mm. Texture: Moderate to smooth. Color: RHS 145A (Strong yellow green). Attitude of hairs: Upwards.
*Petiolule.*—Length: 12 mm. Diameter: 2 mm. Texture: Smooth. Color: RHS 145A (Strong yellow green).
*Stipule.*—Number: 1 per leaf. Shape: Triangular. Shape of apex: Obtuse. Shape of base: Truncate Margin: Smooth.. Length: 44 mm. Width: 22 mm. Texture: Moderate to smooth. Color: RHS 145C (Light yellow green). Anthocyanin coloration: Medium Anthocyanin color: RHS 184B (Moderate red)..

Inflorescence:

*Average number of flowers per peduncle.*—11.8.
*Position of inflorescence in relation to foliage.*—Clearly beneath.
*Length.*—21 cm.
*Width.*—5 cm.
*Longevity.*—7-9 days.
*Peduncle.*—Length: 5 cm. Diameter: 2 mm. Texture: Moderate to smooth Color: RHS N144C (Strong yellow green)..
Pedicel.—Length: 4 cm. Diameter: 1.8 mm. Texture: Moderate to smooth. Color: RHS N144C (Strong yellow green).

*Bract*.—Number: 1. Length: 6 cm. Width: 4 cm. Shape: Obovate. Shape of apex: Obtuse. Shape of base: Ovate. Margin: Serrate. Texture of upper surface: Moderate to smooth. Texture of lower surface: Moderate to smooth. Color of upper surface: RHS 146D (Moderate yellow green). Color of lower surface: RHS 144A (Strong yellow green).

*Bud*.—Shape: Pyriform. Length: 10 mm. Diameter: 5 mm. Texture: Moderate. Color: RHS 144C (Strong yellow green).

*Flower*.—Flower diameter: Medium to large; 30 mm. Height/Depth: 10 mm. Arrangement of petals: Touching. Calyx diameter: 35 mm. Size of calyx in relation to corolla: Larger. Stamen: Present. Number of flowers per plant per season: 100 flowers. Aspect: Upward. Fragrance: None.

*Sepal*.—Number: 5-7. Length: 2.5 cm. Width: 2.1 cm Shape: Cuneate.. Shape of apex: Obtuse. Shape of base: Ovate. Margin: Smooth. Texture of upper surface: Moderate to smooth. Texture of lower surface: Moderate to smooth. Color of upper surface: RHS 137A (Moderate olive green). Color of lower surface: RHS 137C (Moderate yellow green).

*Reproductive organs*.—Stamen number: 21. Filament: Length: 3 mm. Color: RHS 145D (Light yellow green). Anther: Shape: Ovoid. Length: 2 mm. Width: 1.5 mm. Color: RHS 16A (Vivid yellow). Pollen: Amount: Abundant. Color: RHS 16A (Vivid yellow). Pistil: Number: 300. Length: 1 mm. Color: RHS 4D (Pale yellow green). Style: Length: 0-1 mm. Color: RHS 1A (Brilliant greenish yellow). Stigma: Shape: Simple. Diameter: 0.1 mm Color: RHS 4D (Pale yellow green).. Ovary: Color: RHS 1D (Pale greenish yellow).

*Petal*.—Number: 5-6. Length: 2.1 cm. Width: 1.9 cm. Length/width ratio: High. Shape of apex: Obtuse. Shape of base: Decurrent. Margin: Smooth. Texture of upper surface: Smooth. Texture of lower surface: Smooth. Color of upper surface: RHS NN155D (White). Color of lower surface: RHS NN155D (White). Overall shape: Elliptic

*Flowering*.—Flowering runners: Present. Flowering season: Winter. Date of beginning of flowering: Early October. Blooming period: 8 months.

Fruit:

*Number produced per plant per season*.—50 fruits.

*Fruit size*.—Overall size: Very large. Average fruit weight: 25 g. Average fruit length: 54 mm. Average fruit diameter: 36 mm. Maximum fruit weight: 75 g. Maximum fruit length: 86.32 mm. Maximum fruit diameter: 46.87 mm. Position of maximum diameter: Moderately towards the calyx.

*Shape*.—Conical.

*Shape of apex*.—Acute.

*Shape at calyx end*.—Rounded.

*Significant difference between primary and secondary fruit shape*.—Absent.

*Fruit cavity*.—Absent.

*Fruit color*.—RHS 34A (Vivid reddish orange).

*Glossiness*.—Strong.

*Width of band without achenes*.—Very narrow to narrow.

*Position of achenes*.—Level with surface.

*Position of calyx attachment*.—Level with fruit.

*Adherence to calyx*.—Strong.

*Attitude of sepals*.—Outwards.

*Diameter of calyx in relation to diameter of fruit*.—Slightly larger.

*Firmness*.—Firm (232 g·mm-2).

*Color of flesh* (*excluding core*).—RHS 46D (Deep yellowish pink).

*Color of core*.—RHS 48D (Strong pink).

*Average sweetness*.—11.5 Brix.

*Achenes*.—Number per berry: 150-200. Length: 2 mm. Width: 0.8 mm. Weight: 0.8 mg. Color of upper (sunward) side: RHS 153B (Strong greenish yellow). Color of lower (shaded) side: RHS 187B (Dark red).

*Fruiting*.—Time of beginning of fruit ripening: November 10. Fruiting season: 6 months; November-April. Marketable yield per season: 800 g per plant per season. Postharvest fruit longevity: 2-7 days at room temperature; 30 days if refrigerated. Fruit shipping quality: Good.

COMPARISON WITH PARENTAL AND REFERENCE VARIETIES

'HongHui' differs from the female parent 'H2' (cross-breed of 'Tokun' (South Korean Plant Variety Protection Application No. 2013-9; Japanese Plant Variety Protection Registration No. 21165) and 'Sulhyang' (South Korean Plant Variety Protection Application No. 2012-427)) in that 'HongHui' pollinates well and produces larger fruit than 'H2'. Moreover, the leaves of variety 'HongHui' are larger than the leaves of 'H2'. In addition, 'HongHui' produces fruit with a medium red color, while 'H2' produces fruit with a light pink color. Further, 'HongHui' plants have less resistance to powdery mildew than 'H2' plants.

'HongHui' differs from the male parent 'Kingsberry' (South Korean Plant Variety Protection Application No. 2016-319) in that the fruits produced by 'HongHui' are more firm and have higher acidity than the fruits produced by 'Kingsberry'. Moreover, 'HongHui' produces fruit with a larger maximum diameter than the fruits of 'Kingsberry'. In addition, 'HongHui' plants are more vigorous than 'Kingsberry' plants. Further, the leaves of 'HongHui' are larger than the leaves of 'Kingsberry'. While the first peduncle (flush) of 'HongHui' happens around the same time as the first peduncle of 'Kingsberry', the second peduncle of 'HongHui' comes out faster than the second peduncle of 'Kingsberry'. Additionally, the 'HongHui' plants have higher resistance to anthracnose, *Fusarium* wilt (*Fusarium oxysporum*), and *Phytophthora* blight than 'Kingsberry' plants.

'HongHui' differs from the commercial variety 'Sulhyang' (South Korean Plant Varity Protection Certificate No. 2012-427) in that 'HongHui' produces very large fruit, while 'Sulhyang' produces large fruit. Additionally, the fruit of 'HongHui' has strong glossiness, while the fruit of 'Sulhyang' has medium glossiness. Moreover, 'HongHui' plants have strong vigor, while 'Sulhyang' plants have medium vigor. Further, 'HongHui' produces larger flowers than 'Sulhyang'. In addition, 'HongHui' plants produce flower trusses consistently at a faster rate than 'Sulhyang' plants. Furthermore, the leaves of 'HongHui' are very large, while the leaves of 'Sulhyang' are medium in size. Moreover, the fruit of 'HongHui' has a small or absent hollow center, while the fruit of 'Sulhyang' has a medium hollow center. Further, the time of fruit maturation is very slow for 'HongHui', while the time of fruit maturation for 'Sulhyang' is fast.

I claim:

1. A new and distinct variety of strawberry plant named 'HongHui' as shown and described herein.

* * * * *